(12) United States Patent
Abedin et al.

(10) Patent No.: US 11,967,067 B2
(45) Date of Patent: Apr. 23, 2024

(54) DISEASE DETECTION WITH MASKED ATTENTION

(71) Applicant: Merative US L.P., Ann Arbor, MI (US)

(72) Inventors: Shafiqul Abedin, San Jose, CA (US); Hongzhi Wang, Santa Bruno, CA (US); Ehsan Dehghan Marvast, Palo Alto, CA (US); David James Beymer, San Jose, CA (US)

( * ) Notice: Subject to any disclaimer, the term of this patent is extended or adjusted under 35 U.S.C. 154(b) by 455 days.

(21) Appl. No.: 17/319,606

(22) Filed: May 13, 2021

(65) Prior Publication Data

US 2022/0375068 A1    Nov. 24, 2022

(51) Int. Cl.
*G06T 7/00* (2017.01)
*G06F 18/2433* (2023.01)
(Continued)

(52) U.S. Cl.
CPC ........ *G06T 7/0012* (2013.01); *G06F 18/2433* (2023.01); *G06N 3/045* (2023.01); *G06N 3/08* (2013.01); *G06T 7/11* (2017.01); *G06V 10/34* (2022.01); *G16H 30/20* (2018.01); *G16H 30/40* (2018.01); *G16H 50/20* (2018.01);
(Continued)

(58) Field of Classification Search
CPC .................. G06T 7/0012; G06T 7/11; G06T 2207/20081; G06T 2207/20084; G06T 2207/10081; G06T 2207/30061; G06F 18/2433; G06N 3/045; G06N 3/08; G06N 3/048; G06N 3/0464; G06N 3/09; G06V 10/34; G06V 10/454; G06V 10/82;
(Continued)

(56) References Cited

U.S. PATENT DOCUMENTS 8,244,012 B2  8/2012  Liang et al.
9,959,615 B2  5/2018  Liang et al.
(Continued)

OTHER PUBLICATIONS

Forrest Iandola et al. Squeezenet: Alexnet-Level Accuracy With 50X Fewer Parameters and <0.5MB Model (Year: 2017).*
(Continued)

*Primary Examiner* — Dhaval V Patel
(74) *Attorney, Agent, or Firm* — Stephen J. Walder, Jr.

(57) ABSTRACT

A candidate generator generates a set of candidate three-dimensional image patches from an input volume. A candidate classifier classifies the set of candidate three-dimensional image patches as containing or not containing disease. Classifying the set of candidate three-dimensional image patches comprises generating an attention mask for each given candidate three-dimensional image patch within the set of candidate three-dimensional image patches to form a set of attention masks, applying the set of attention masks to the set of candidate three-dimensional image patches to form a set of masked image patches, and classifying the set of masked image patches as containing or not containing the disease. The candidate classifier applies soft attention and hard attention to the three-dimensional image patches such that distinctive image regions are highlighted proportionally to their contribution to classification while completely removing image regions that may cause confusion.

20 Claims, 3 Drawing Sheets
(1 of 3 Drawing Sheet(s) Filed in Color)

(51) Int. Cl.
| | |
|---|---|
| *G06N 3/045* | (2023.01) |
| *G06N 3/08* | (2023.01) |
| *G06T 7/11* | (2017.01) |
| *G06V 10/34* | (2022.01) |
| *G16H 30/20* | (2018.01) |
| *G16H 30/40* | (2018.01) |
| *G16H 50/20* | (2018.01) |

(52) U.S. Cl.
CPC .............. *G06T 2207/20081* (2013.01); *G06T 2207/20084* (2013.01)

(58) Field of Classification Search
CPC .. G06V 2201/031; G16H 30/20; G16H 30/40; G16H 50/20; G16H 50/30
See application file for complete search history.

(56) References Cited

U.S. PATENT DOCUMENTS

| | | | | |
|---|---|---|---|---|
| 11,425,448 | B1* | 8/2022 | Khot | H04N 5/765 |
| 2021/0398654 | A1* | 12/2021 | Chaganti | G16H 50/80 |
| 2022/0309653 | A1* | 9/2022 | Hassanpour | G06V 10/82 |

OTHER PUBLICATIONS

Barritt, D.W. et al., "Anticoagulant drugs in the treatment of pulmonary embolism. A controlled trial.", The Lancet, vol. 275, Issue 7138, Jun. 18, 1960, 4 pages.

Buhmann, Sonja et al., "Clinical evaluation of a computer-aided diagnosis (CAD) prototype for the detection of pulmonary embolism", Academic Radiology, vol. 14, Issue 6, Jun. 2007, 3 pages. (Abstract only).

Carson, Jeffrey L. et al., "The Clinical Course of Pulmonary Embolism", New England Journal of Medicine, May 7, 1992, 6 pages.

Coon, William W. et al., "Assessment of Anticoagulant Treatment of Venous Thromboembolism".

Dai, Jifeng et al., "Convolutional Feature Masking for Joint Object and Stuff Segmentation", 2015 IEEE Conference on Computer Vision and Pattern Recognition (CVPR), Jun. 2015, 9 pages.

Dalen, James E. et al., "Natural history of pulmonary embolism", Progress in Cardiovascular Diseases, vol. 17, Issue 4, Jan.-Feb. 1975, p. 1 only.

Das, Marco et al., "Computer-aided detection of pulmonary embolism: Influence on radiologists' detection performance with respect to vessel segments", European radiology, vol. 18, Feb. 2008, 6 pages.

Engelke, Christoph et al., "Computer-assisted detection of pulmonary embolism: performance evaluation in consensus with experienced and inexperienced chest radiologists", European radiology vol. 18, Feb. 2008, 3 pages. (Abstract only).

Hermann, Robert E. et al., "Pulmonary embolism. A clinical and pathologic study with emphasis on the effect of prophylactic therapy with anticoagulants", The American Journal of Surgery, vol. 102, Issue 1, Jul. 1961, Abstract only.

Huang, Shih-Cheng et al., "PENet—a scalable deep-learning model for automated diagnosis of pulmonary embolism using volumetric CT imaging", NPJ Digital Medicine vol. 3, Article 61, Apr. 24, 2020, 9 pages.

Iandola, Forrest N. et al., "Squeezenet: Alexnet-Level Accuracy With 50X Fewer Parameters and <0.5MB Model Size", arXiv:1602.07360v4 [cs.CV] Nov. 4, 2016, 13 pages.

Liang, Jianming et al., "Computer Aided Detection of Pulmonary Embolism with Tobogganing and Mutiple Instance Classification in CT Pulmonary Angiography", 20th International Conference, IPMI 2007, Jul. 2-6, 2007, 12 pages.

Milletari, Fausto et al., "V-Net: Fully Convolutional Neural Networks for Volumetric Medical Image Segmentation", 2016 Fourth International Conference, on 3D Vision (3DV), Oct. 2016, 11 pages.

Mnih, Volodymyr et al., "Recurrent Models of Visual Attention", arXiv:1406.6247v1 [cs.LG] Jun. 24, 2014, 12 pages.

Morrell, M. Tessa et al., "The post-mortem incidence of pulmonary embolism in a hospital population", British Journal of Surgery, vol. 55, Issue 5, May 1968, p. one only.

Ronneberger, Olaf et al., "U-Net: Convolutional Networks for Biomedical Image Segmentation", International Conference on Medical image computing and computer-assisted intervention, Oct. 5-9, 2015, 8 pages.

Schoepf, Joseph U. et al., "Pulmonary embolism: computer-aided detection at multidetector row spiral computed tomography", Journal of Thoracic Imaging: Nov. 2007—vol. 22—Issue 4, (Abstract Only).

Tao, Qingyi et al., "Improving Deep Lesion Detection Using 3D Contextual and Spatial Attention", arXiv:1907.04052v1 [cs.CV] Jul. 9, 2019, 10 pages.

Zhou, Chuan et al., "Preliminary investigation of computer-aided detection of pulmonary Pulmonary Embolism in Threedimensional Computed Tomography Pulmonary Angiography Images", Academic radiology vol. 12, Jun. 2005, 19 pages.

Gonzalez, German et al., "Computer Aided Detection for Pulmonary Embolism Challenge (CAD-PE)", arXiv preprint arXiv: 2003.13440., Aug. 2019, 8 pages.

Kashyap, Satyananda et al., "Looking in the Right Place for Anomalies: Explainable AI Through Automatic Location Learning", 2020 International Symposium on Biomedical Imaging (ISBI), Apr. 3-7, 2020, submitted version arXiv: 2008.00363v1 [cs.CV] Aug. 2, 2020, 6 pages.

Lee, Matthew C. et al., "Image-and-Spatial Transformer Networks for Structure-Guided Image Registration", arXiv: 1907.09200v1 [cs.CV] Jul. 22, 2019, 9 pages.

Ma, Jiechao et al., "Survey on deep learning for pulmonary medical imaging", Front. Med. 14, 450-469 (2020). https://doi.org/10.1007/s11684-019-0726-4, Published Dec. 16, 2019, 20 pages.

Rajan, Deepta et al., "Pi-PE: A Pipeline for Pulmonary Embolism Detection using Sparsely Annotated 3D CT Images", Proceedings of Machine Learning Research, 2019 Machine Learning for Health (ML4H) at NeurIPS 2019, Dec. 2019, 13 pages.

Schlemper, Jo et al., "Attention gated networks: Learning to leverage salient regions in medical images", Medical Image Analysis, vol. 53, Apr. 2019, pp. 197-207.

Shi, Luyao et al., "Automatic Diagnosis of Pulmonary Embolism Using an Attention-guided Framework: A Large-scale Study", arXiv: 2006.00074v1 [eess.IV] May 29, 2020, 12 pages.

Tajbakhsh, Nima et al., "Computer-aided Pulmonary Embolism Detection Using a Novel Vessel-Aligned Multi-Planar Image Representation and Convolutional Neural Networks", Conference: International Conference on Medical Image Computing and Computer-Assisted Intervention, Oct. 2015, 8 pages.

Wang, Fei et al., "Residual Attention Network for Image Classification", arXiv: 1704.06904v1 [cs.CV] Apr. 23, 2017, 9 pages.

Yang, Xin et al., "A Two-Stage Convolutional Neural Network for Pulmonary Embolism Detection From CTPA Images", https://ieeexplore.ieee.org/stamp/stamp.jsp?arnumber=8746218, Jul. 2019, 9 pages.

* cited by examiner

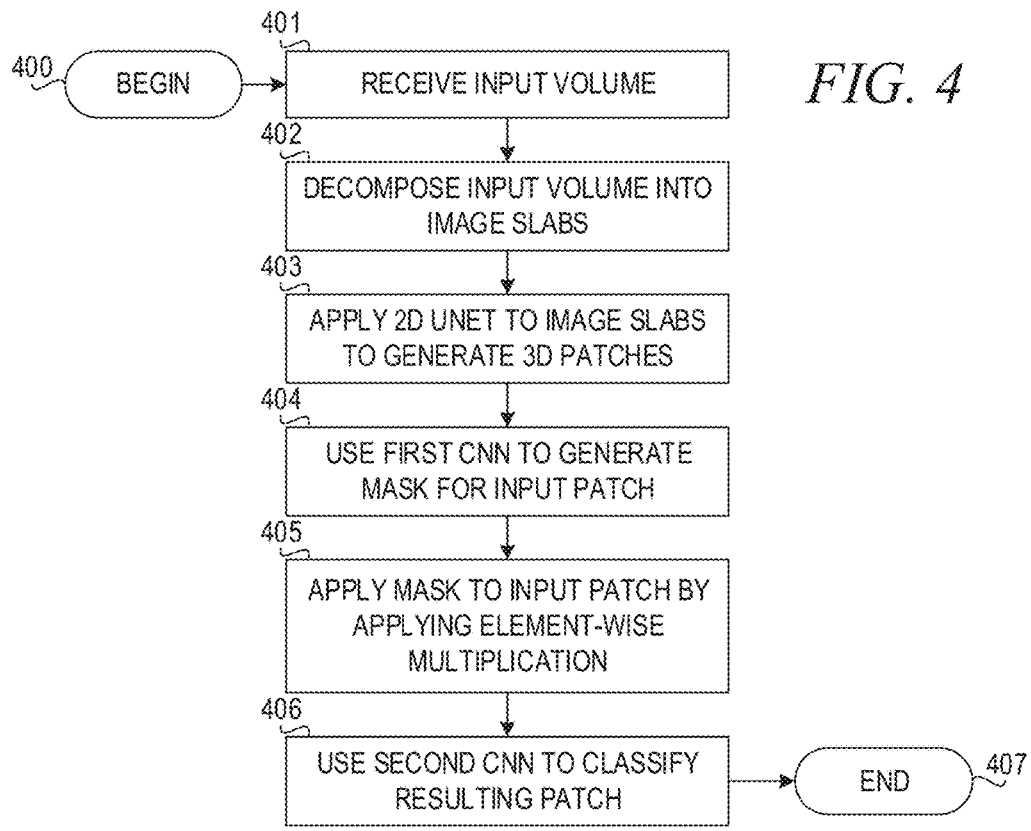
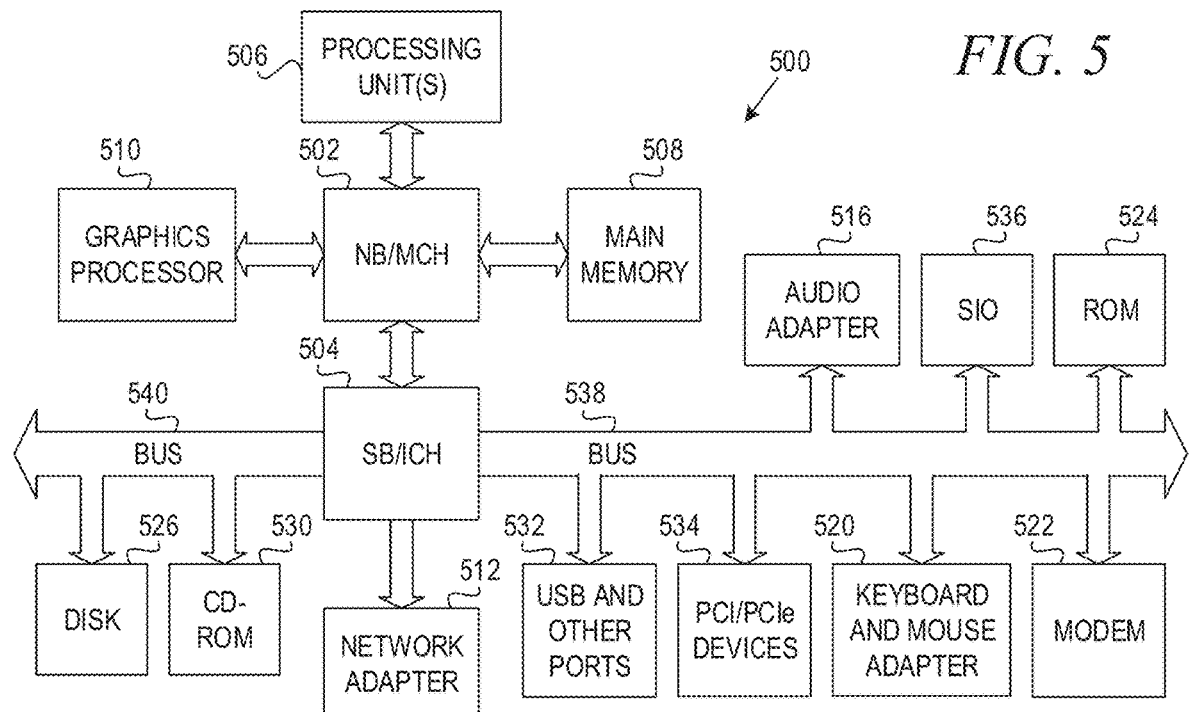

DISEASE DETECTION WITH MASKED ATTENTION

BACKGROUND

The present application relates generally to an improved data processing apparatus and method and more specifically to mechanisms for computer aided disease detection with masked attention.

Detecting clinically evident Pulmonary Embolism (PE) is important in quickly diagnosing patients with symptoms and signs of venous thromboembolism. Untreated clinically apparent PE has a nearly 30% mortality rate in contrast to an 8% mortality rate for those patients who receive treatment. Although the mortality rate from PE alone is only 2.5%, timely detection and anticoagulation therapy improves the patient's outcome.

Patients suspected of PE are recommended to take a D-Dimer test followed by a CT Pulmonary Angiography (CTPA) for high probability clinical assessment. A radiologist must carefully inspect each branch of the pulmonary arteries for suspected PE. Consequently, diagnosis of PE hinges on the radiologist's experience, attention span and eye fatigue, among others. Computer Aided Detection (CAD) software for PE detection has historically shown to help radiologists detect and diagnose PE. However, in order to minimize the interference of the radiologist's reading, it is highly desirable to have a CAD system with a lower false positive rate. In addition, detecting PE in CT angiography (CTA) images can be useful in a retrospective setup where the CAD software is used to detect missed findings.

SUMMARY

This Summary is provided to introduce a selection of concepts in a simplified form that are further described herein in the Detailed Description. This Summary is not intended to identify key factors or essential features of the claimed subject matter, nor is it intended to be used to limit the scope of the claimed subject matter.

In one illustrative embodiment, a method is provided in a data processing system, for computer aided disease detection with masked attention. The method comprises generating, by a candidate generator, a set of candidate three-dimensional image patches from an input volume. The method further comprises classifying, by a candidate classifier, the set of candidate three-dimensional image patches as containing or not containing disease. Classifying the set of candidate three-dimensional image patches comprises generating an attention mask for each given candidate three-dimensional image patch within the set of candidate three-dimensional image patches to form a set of attention masks, applying the set of attention masks to the set of candidate three-dimensional image patches to form a set of masked image patches, and classifying the set of masked image patches as containing or not containing the disease. The candidate classifier applies soft attention and hard attention to the three-dimensional image patches such that distinctive image regions are highlighted proportionally to their contribution to classification while completely removing image regions that may cause confusion.

In other illustrative embodiments, a computer program product comprising a computer useable or readable medium having a computer readable program is provided. The computer readable program, when executed on a computing device, causes the computing device to perform various ones of, and combinations of, the operations outlined above with regard to the method illustrative embodiment.

In yet another illustrative embodiment, a system/apparatus is provided. The system/apparatus may comprise one or more processors and a memory coupled to the one or more processors. The memory may comprise instructions which, when executed by the one or more processors, cause the one or more processors to perform various ones of, and combinations of, the operations outlined above with regard to the method illustrative embodiment.

These and other features and advantages of the present invention will be described in, or will become apparent to those of ordinary skill in the art in view of, the following detailed description of the example embodiments of the present invention.

BRIEF DESCRIPTION OF THE DRAWINGS

The patent or application file contains at least one drawing executed in color. Copies of this patent or patent application publication with color drawing(s) will be provided by the Office upon request and payment of the necessary fee.

The invention, as well as a preferred mode of use and further objectives and advantages thereof, will best be understood by reference to the following detailed description of illustrative embodiments when read in conjunction with the accompanying drawings, wherein:

FIG. 4 is a flowchart illustrating operation of a computer aided disease detection engine with masked attention in accordance with an illustrative embodiment; and FIG. 5 is a block diagram of just one example data processing system in which aspects of the illustrative embodiments may be implemented;

DETAILED DESCRIPTION

Figure 1:
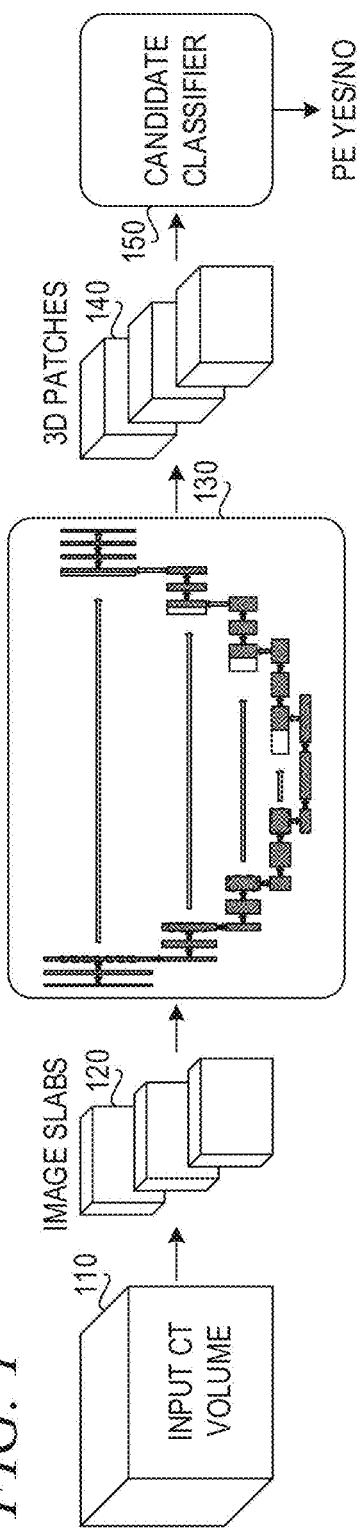
FIG. 1 shows the overall architecture for a computer aided disease detection engine with masked attention in accordance with an illustrative embodiment.

Pulmonary Embolism (PE) usually has small-size, irregular-shaped pathological patterns. Hence, the image region distinctive for PE classification may only account for a small portion of the imaging data even when image patches are used. Localizing the distinctive image region is critical for successful PE classification. Attention-based classification methods address this problem by modifying the input image by applying element-wise multiplication with a soft attention mask before classification. The attention mask has positive values and large/small attention values can be interpreted as boosting/suppressing contributions from the corresponding image regions, respectively. Although image regions not useful for classification are de-emphasized with soft attention, they may still dilute the useful information and cause unnecessary confusion. This problem is more prominent when the distinctive region only accounts for a small portion of the imaging data. Recent work suggests that using a hard mask to remove irrelevant regions can improve classification performance. The illustrative embodiments propose to combine soft attention with hard attention such that distinctive image regions are highlighted proportionally to their contribution to classification while completely removing image regions that may cause confusion.

Before beginning the discussion of the various aspects of the illustrative embodiments and the improved computer operations performed by the illustrative embodiments, it should first be appreciated that throughout this description the term "mechanism" will be used to refer to elements of the present invention that perform various operations, functions, and the like. A "mechanism," as the term is used herein, may be an implementation of the functions or aspects of the illustrative embodiments in the form of an apparatus, a procedure, or a computer program product. In the case of a procedure, the procedure is implemented by one or more devices, apparatus, computers, data processing systems, or the like. In the case of a computer program product, the logic represented by computer code or instructions embodied in or on the computer program product is executed by one or more hardware devices in order to implement the functionality or perform the operations associated with the specific "mechanism." Thus, the mechanisms described herein may be implemented as specialized hardware, software executing on hardware to thereby configure the hardware to implement the specialized functionality of the present invention which the hardware would not otherwise be able to perform, software instructions stored on a medium such that the instructions are readily executable by hardware to thereby specifically configure the hardware to perform the recited functionality and specific computer operations described herein, a procedure or method for executing the functions, or a combination of any of the above.

The present description and claims may make use of the terms "a", "at least one of", and "one or more of" with regard to particular features and elements of the illustrative embodiments. It should be appreciated that these terms and phrases are intended to state that there is at least one of the particular feature or element present in the particular illustrative embodiment, but that more than one can also be present. That is, these terms/phrases are not intended to limit the description or claims to a single feature/element being present or require that a plurality of such features/elements be present. To the contrary, these terms/phrases only require at least a single feature/element with the possibility of a plurality of such features/elements being within the scope of the description and claims.

Moreover, it should be appreciated that the use of the term "engine," if used herein with regard to describing embodiments and features of the invention, is not intended to be limiting of any particular implementation for accomplishing and/or performing the actions, steps, processes, etc., attributable to and/or performed by the engine. An engine may be, but is not limited to, software executing on computer hardware, specialized computer hardware and/or firmware, or any combination thereof that performs the specified functions including, but not limited to, any use of a general and/or specialized processor in combination with appropriate software loaded or stored in a machine readable memory and executed by the processor to thereby specifically configure the processor to perform the specific functions of the illustrative embodiments. Further, any name associated with a particular engine is, unless otherwise specified, for purposes of convenience of reference and not intended to be limiting to a specific implementation. Additionally, any functionality attributed to an engine may be equally performed by multiple engines, incorporated into and/or combined with the functionality of another engine of the same or different type, or distributed across one or more engines of various configurations.

In addition, it should be appreciated that the following description uses a plurality of various examples for various elements of the illustrative embodiments to further illustrate example implementations of the illustrative embodiments and to aid in the understanding of the mechanisms of the illustrative embodiments. These examples intended to be non-limiting and are not exhaustive of the various possibilities for implementing the mechanisms of the illustrative embodiments. It will be apparent to those of ordinary skill in the art in view of the present description that there are many other alternative implementations for these various elements that may be utilized in addition to, or in replacement of, the examples provided herein without departing from the spirit and scope of the present invention.

The present invention may be a system, a method, and/or a computer program product. The computer program product may include a computer readable storage medium (or media) having computer readable program instructions thereon for causing a processor to carry out aspects of the present invention.

The computer readable storage medium can be a tangible device that can retain and store instructions for use by an instruction execution device. The computer readable storage medium may be, for example, but is not limited to, an electronic storage device, a magnetic storage device, an optical storage device, an electromagnetic storage device, a semiconductor storage device, or any suitable combination of the foregoing. A non-exhaustive list of more specific examples of the computer readable storage medium includes the following: a portable computer diskette, a hard disk, a random access memory (RAM), a read-only memory (ROM), an erasable programmable read-only memory (EPROM or Flash memory), a static random access memory (SRAM), a portable compact disc read-only memory (CD-ROM), a digital versatile disk (DVD), a memory stick, a floppy disk, a mechanically encoded device such as punch-cards or raised structures in a groove having instructions recorded thereon, and any suitable combination of the foregoing. A computer readable storage medium, as used herein, is not to be construed as being transitory signals per se, such as radio waves or other freely propagating electromagnetic waves, electromagnetic waves propagating through a waveguide or other transmission media (e.g., light pulses passing through a fiber-optic cable), or electrical signals transmitted through a wire.

Computer readable program instructions described herein can be downloaded to respective computing/processing devices from a computer readable storage medium or to an external computer or external storage device via a network, for example, the Internet, a local area network, a wide area network and/or a wireless network. The network may comprise copper transmission cables, optical transmission fibers, wireless transmission, routers, firewalls, switches, gateway computers and/or edge servers. A network adapter card or network interface in each computing/processing device receives computer readable program instructions from the network and forwards the computer readable program instructions for storage in a computer readable storage medium within the respective computing/processing device.

Computer readable program instructions for carrying out operations of the present invention may be assembler instructions, instruction-set-architecture (ISA) instructions, machine instructions, machine dependent instructions, microcode, firmware instructions, state-setting data, or either source code or object code written in any combination of one or more programming languages, including an object oriented programming language such as Java, Smalltalk, C++ or the like, and conventional procedural programming languages, such as the "C" programming language or similar programming languages. The computer readable program instructions may execute entirely on the user's computer, partly on the user's computer, as a stand-alone software package, partly on the user's computer and partly on a remote computer or entirely on the remote computer or server. In the latter scenario, the remote computer may be connected to the user's computer through any type of network, including a local area network (LAN) or a wide area network (WAN), or the connection may be made to an external computer (for example, through the Internet using an Internet Service Provider). In some embodiments, electronic circuitry including, for example, programmable logic circuitry, field-programmable gate arrays (FPGA), or programmable logic arrays (PLA) may execute the computer readable program instructions by utilizing state information of the computer readable program instructions to personalize the electronic circuitry, in order to perform aspects of the present invention.

Aspects of the present invention are described herein with reference to flowchart illustrations and/or block diagrams of methods, apparatus (systems), and computer program products according to embodiments of the invention. It will be understood that each block of the flowchart illustrations and/or block diagrams, and combinations of blocks in the flowchart illustrations and/or block diagrams, can be implemented by computer readable program instructions.

These computer readable program instructions may be provided to a processor of a computer or other programmable data processing apparatus to produce a machine, such that the instructions, which execute via the processor of the computer or other programmable data processing apparatus, create means for implementing the functions/acts specified in the flowchart and/or block diagram block or blocks. These computer readable program instructions may also be stored in a computer readable storage medium that can direct a computer, a programmable data processing apparatus, and/or other devices to function in a particular manner, such that the computer readable storage medium having instructions stored therein comprises an article of manufacture including instructions which implement aspects of the function/act specified in the flowchart and/or block diagram block or blocks.

The computer readable program instructions may also be loaded onto a computer, other programmable data processing apparatus, or other device to cause a series of operational steps to be performed on the computer, other programmable apparatus or other device to produce a computer implemented process, such that the instructions which execute on the computer, other programmable apparatus, or other device implement the functions/acts specified in the flowchart and/or block diagram block or blocks.

The flowchart and block diagrams in the Figures illustrate the architecture, functionality, and operation of possible implementations of systems, methods, and computer program products according to various embodiments of the present invention. In this regard, each block in the flowchart or block diagrams may represent a module, segment, or portion of instructions, which comprises one or more executable instructions for implementing the specified logical function(s). In some alternative implementations, the functions noted in the block may occur out of the order noted in the figures. For example, two blocks shown in succession may, in fact, be executed substantially concurrently, or the blocks may sometimes be executed in the reverse order, depending upon the functionality involved. It will also be noted that each block of the block diagrams and/or flowchart illustration, and combinations of blocks in the block diagrams and/or flowchart illustration, can be implemented by special purpose hardware-based systems that perform the specified functions or acts or carry out combinations of special purpose hardware and computer instructions.

Computer aided detection of PE has been developed to aid radiologists better detect emboli, especially small segmental and subsegmental emboli, and to improve negative and positive predictive scores. Successful CAD systems for PE primarily consists of two stages: 1) candidate generation using either a rule-based algorithm (i.e., tobogganing) or deep learning-based segmentation, and 2) classification of candidates using a rule-based classifier, neural networks, or multi-instance classifier. The illustrative embodiments take a two-stage approach, using deep learning-based methods for both stages.

Although soft attention is more commonly applied in the prior art, hard attention has been applied as well. In one prior art approach, a region proposal mechanism is combined with region cropping to obtain image patch representations for localized analysis. In this approach, only binary attention masks with regular shapes, i.e., rectangle shapes, are used for patch cropping. In another approach, binary masks with irregular shapes that more accurately align with the object of interest are applied to exclude irrelevant regions from consideration and has shown to be effective for object classification. However, the mask was generated via a region proposal method that groups super-pixel segments produced by bottom-up segmentation.

Since the bottom-up segmentation is pre-computed and is not optimized during training, the obtained mask is limited by the pre-computed segments and may not be optimal for the classification task. Compared to previous methods using hard attention, the key advantage of the illustrative embodiments is that the attention mask is learned automatically for optimal classification. Like attention-based methods, the image transformer network approach transforms images by multiplying them with transform maps. However, unlike the illustrative embodiments where only non-negative transform maps are applied, the image transformer network approach has no constraints on the produced transforms and has less clear attention interpretation.

Since PE has localized features, the illustrative embodiments apply patch-based classification for PE detection. To make patch-based detection more efficient and more accurate, the illustrative embodiments first use PE segmentation to localize embolism candidates. At inference, patient-level PE classification score is obtained by choosing the maximum PE classification score for all candidate patches.

FIG. 1 shows the overall architecture for a computer aided disease detection engine with masked attention in accordance with an illustrative embodiment. The computer aided image-based disease detection engine shown in FIG. 1 comprises a two-stage pipeline for efficient disease detection: candidate generation and candidate classification. Input computerized tomography (CT) volume 110 is broken up into image slabs 120, which are provided to candidate generator 130. In the depicted example, candidate generator 130 uses a 2D U-Net to generate 3D patches 140, which represent the disease candidates. 3D patches 140 are classified as containing the disease if and only if at least one of the disease candidates is classified as containing the disease.

For more efficient detection, the computer aided disease detection engine applies PE segmentation to identify embolus candidates. Since the clinician-based PE annotations of segmented polygons were produced on sparse 2D slices, the computer aided disease detection engine uses a slab-based 2D segmentation method using two-dimensional U-Net 130. Instead of using only 2D slices, a slab of nine slices 120 is fed to the network 130 with the corresponding binary mask as the ground truth. The U-Net model 130 in the segmentation task consists of 70 layers with a contracting path with repeated 3×3 convolutions, each followed by rectified linear unit (ReLU) and a 2×2 max pooling operations with a stride of 2 for down-sampling. The expansive path consists of up-sampling of features followed by a 2×2 convolution, concatenation with the correspondingly cropped feature map from the contracting path and 3×3 convolutions, each followed by a ReLU. The probability map is computed by a pixel-wise softmax over the final feature map. For training, the continuous dice loss (DL) function is applied. In the illustrative embodiments, only the middle slice of the slab is considered to compute the dice.

PE segmentation identifies potential PE candidates. Given an output PE segmentation, connected components are computed, and each connected component is a PE candidate. 3D cubic patches 140 are then extracted to represent PE candidates. These 3D cubic patches 140 are fed into candidate classifier 150. In accordance with the illustrative embodiment, candidate classifier 150 generates a mask for the input patch using a convolutional neural network (CNN), applies the mask to the input patch by applying element-wise multiplication, and classifies the resulting patch by a second CNN. The first and second CNNs are trained jointly. Candidate classifier 150 classifies each of the 3D cubic patches 140 as containing a PE or not.

Figure 2:
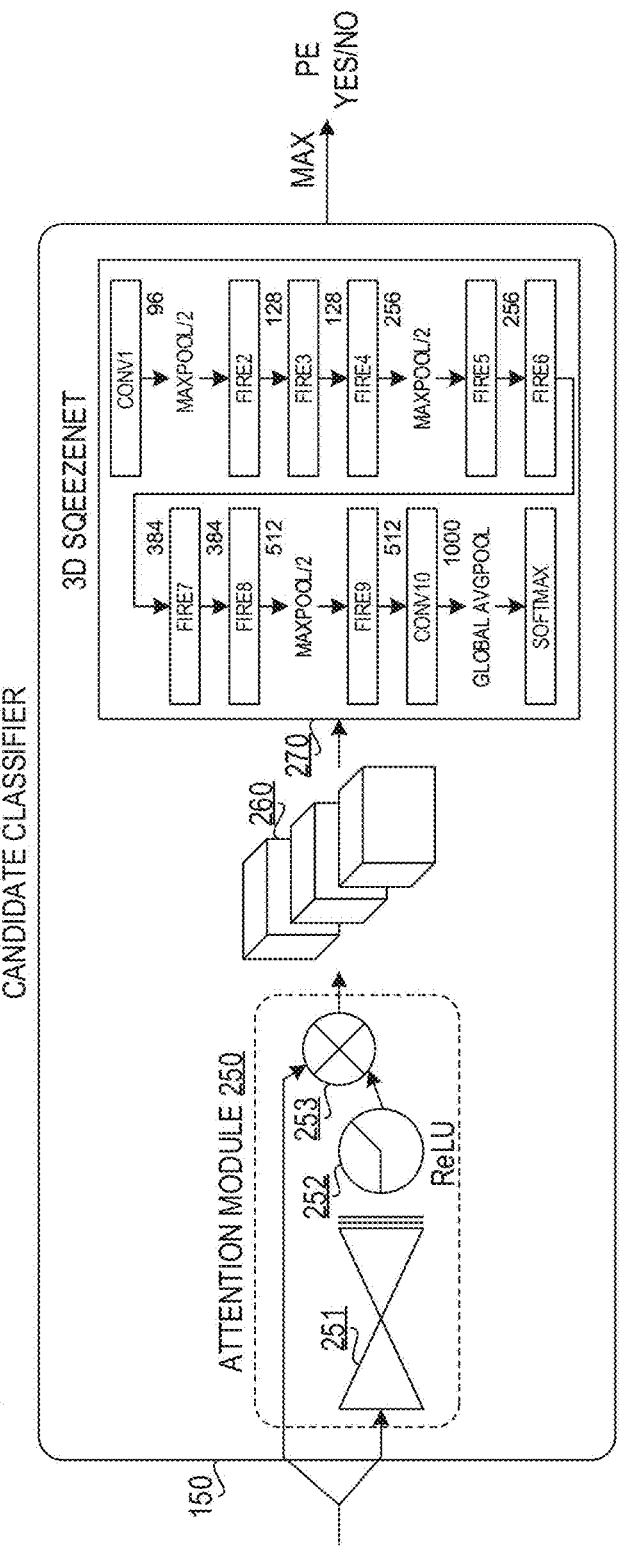
FIG. 2 shows the architecture of the candidate classifier in accordance with an illustrative embodiment.

FIG. 2 shows the architecture of the candidate classifier in accordance with an illustrative embodiment. Candidate classifier 150 comprises attention module 250, which generates an attention mask for the input patch and applies the attention mask to the input patch to generate masked 3D patches 260. Neural network 251 is a three-dimensional convolutional neural network (CNN). CNN 251 and rectified linear unit (ReLU) function 252 produce the attention mask, as described in further detail below. Multiplier 253 then multiplies the generated attention mask with the input image to generate masked 3D patches. 3D SqueezeNet 270 receives the masked 3D patches and classifies the patches as containing a PE or not containing a PE.

For patch-based PE classification, SqueezeNet 270 is applied. The network starts with a convolution layer, followed by eight Fire modules, and ending with a final convolution layer. The Fire module is a combination of a squeeze convolution layer of 1×1 filters feeding into a expand layer of 1×1×1 and 3×3×3 convolution filters. The energy function is computed by soft-max over the final feature map combined with categorical cross entropy loss. For the classification stage, the SqueezeNet only has 2 classes, positive and negative.

Since PE has large variation in size and shape, the distinctive image region for PE classification may only account for a small portion of the patch representation. The illustrative embodiments propose an attention approach for PE classification. To this end, the illustrative embodiments adapt a 3D U-net model for attention estimation by replacing the last layer with a 1×1 convolution layer to produce one transform map $M \in \mathbb{R}^{L \times L \times L}$, where L×L×L is the size of the input image patch.

In image transformer networks, M is directly applied as a feature representation for downstream classification. In soft attention methods, M is first transferred to a soft attention map A with value range (0, 1) by applying either a sigmoid function or a softmax function. A is then applied via element-wise multiplication 253 with the input image patch for downstream classification. Due to the use of element-wise multiplication 253 and non-negative attention values, large/small attention values can be interpreted as boosting/suppressing contribution of the corresponding image regions for classification, respectively. Note that the image transformer network method can also be reformulated as applying element-wise multiplication between a transform map and the input image patch to obtain the feature representation. However, the transform map used by image transformer networks can have negative values and the attention interpretation is less clear.

Even though less important image regions are de-emphasized by the soft attention approach, they may still dilute the useful information for classification. To avoid this dilution problem, the illustrative embodiments combine the soft attention mask with a hard mask to remove irrelevant regions from consideration. The illustrative embodiments apply a rectified linear unit (ReLU) function 252 to produce the attention map as follows:

$$A(x) = \begin{cases} M(x) & \text{if } M(x) \geq 0 \\ 0 & \text{otherwise} \end{cases}$$

Unlike the commonly used sigmoid/softmax function, which produces soft dense attention maps, the ReLU function produces sparser and simpler representations as it encourages excluding nonessential regions in the produced attention maps. Such representations may benefit classification by reducing interference from distracting features in the excluded regions. Compared to the image transformer network method, the key difference in the illustrative embodiment is that the attention interpretation of the transform map is restored by re-enforcing the non-negative constraint. The attention model 250 is trained jointly with the downstream classification model 270 to learn attention maps optimal for the classification task.

Figure 3:
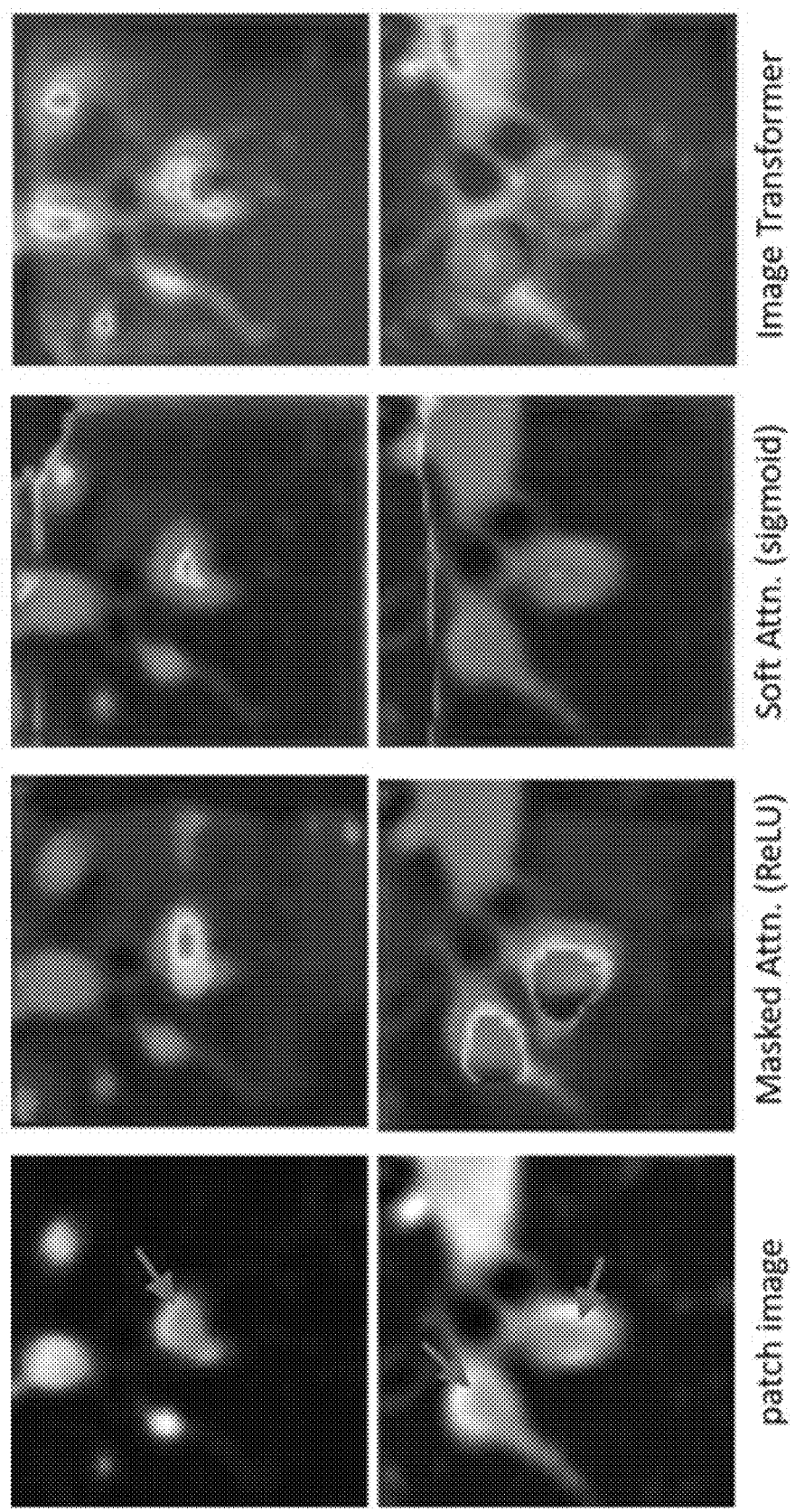
FIG. 3 shows the attention/transform maps produced by different methods with comparison to the computer aided disease detection with masked attention of the illustrative embodiment.

FIG. 3 shows the attention/transform maps produced by different methods with comparison to the computer aided disease detection with masked attention of the illustrative embodiment. In FIG. 3, the results of masked attention (ReLU) of the illustrative embodiments are compared against soft attention (sigmoid function) and an image transformer of prior art approaches. By encouraging to exclude irrelevant regions, the illustrative embodiment produced more focused and more accurate attention than the compared methods. Note that the computer aided disease detection with masked attention of the illustrative embodiment also preserves sufficient contextual regions for the classification task.

FIG. 4 is a flowchart illustrating operation of a computer aided disease detection engine with masked attention in accordance with an illustrative embodiment. Operation begins (block 400), and the computer aided disease detection engine receives an input volume (block 401). The computer aided disease detection engine decomposes the input volume into image slabs (block 402). The computer aided disease detection engine applies a two-dimensional U-Net neural network to the image slabs to generate three-dimensional patches that represent candidate patches (block 403). The computer aided disease detection engine uses a first convolutional neural network to generate a mask for the candidate patch (block 404) and applies the mask by applying an element-wise multiplication (block 405). Next, the computer aided disease detection engine uses a second convolutional neural network to classify the resulting patch as containing or not containing disease (block 406). Thereafter, operation ends (block 407).

Thus, the illustrative embodiments provide an end-to-end pipeline for patient level classification of PE. For efficient and accurate PE detection, illustrative embodiments apply PE segmentation to identify candidate PE regions, which are then classified based on patch representations. The illustrative embodiments propose a masked attention method that combines soft attention and hard attention. The illustrative embodiments produce simpler and more focused representations that not only highlight distinctive image features for classification but also remove irrelevant image regions to avoid confusion. The illustrative embodiments produce more accurate attention maps that lead to more accurate PE detection than commonly used soft attention.

The illustrative embodiments may be utilized in many different types of data processing environments. In order to provide a context for the description of the specific elements and functionality of the illustrative embodiments, FIG. 5 is provided hereafter as an example environment in which aspects of the illustrative embodiments may be implemented. It should be appreciated that FIG. 5 is only an example and is not intended to assert or imply any limitation with regard to the environments in which aspects or embodiments of the present invention may be implemented. Many modifications to the depicted environments may be made without departing from the spirit and scope of the present invention.

As noted above, the mechanisms of the illustrative embodiments utilize specifically configured computing devices, or data processing systems, to perform the operations for computer aided disease detection with masked attention. These computing devices, or data processing systems, may comprise various hardware elements which are specifically configured, either through hardware configuration, software configuration, or a combination of hardware and software configuration, to implement one or more of the systems/subsystems described herein. FIG. 5 is a block diagram of just one example data processing system in which aspects of the illustrative embodiments may be implemented. Data processing system 500 is an example of a computer in which computer usable code or instructions implementing the processes and aspects of the illustrative embodiments of the present invention may be located and/or executed so as to achieve the operation, output, and external effects of the illustrative embodiments as described herein.

In the depicted example, data processing system 500 employs a hub architecture including north bridge and memory controller hub (NB/MCH) 502 and south bridge and input/output (I/O) controller hub (SB/ICH) 504. Processing unit 506, main memory 508, and graphics processor 510 are connected to NB/MCH 502. Graphics processor 510 may be connected to NB/MCH 502 through an accelerated graphics port (AGP).

In the depicted example, local area network (LAN) adapter 512 connects to SB/ICH 504. Audio adapter 516, keyboard and mouse adapter 520, modem 522, read only memory (ROM) 524, hard disk drive (HDD) 526, CD-ROM drive 530, universal serial bus (USB) ports and other communication ports 532, and PCI/PCIe devices 534 connect to SB/ICH 504 through bus 538 and bus 540. PCI/PCIe devices may include, for example, Ethernet adapters, add-in cards, and PC cards for notebook computers. PCI uses a card bus controller, while PCIe does not. ROM 524 may be, for example, a flash basic input/output system (BIOS).

HDD 526 and CD-ROM drive 530 connect to SB/ICH 504 through bus 540. HDD 526 and CD-ROM drive 530 may use, for example, an integrated drive electronics (IDE) or serial advanced technology attachment (SATA) interface. Super I/O (SIO) device 536 may be connected to SB/ICH 504.

An operating system runs on processing unit 506. The operating system coordinates and provides control of various components within the data processing system 500 in FIG. 5. As a client, the operating system may be a commercially available operating system such as Microsoft® Windows 10®. An object-oriented programming system, such as the Java™ programming system, may run in conjunction with the operating system and provides calls to the operating system from Java™ programs or applications executing on data processing system 500.

As a server, data processing system 500 may be, for example, an IBM eServer™ System p® computer system, Power™ processor-based computer system, or the like, running the Advanced Interactive Executive (AIX®) operating system or the LINUX® operating system. Data processing system 500 may be a symmetric multiprocessor (SMP) system including a plurality of processors in processing unit 506. Alternatively, a single processor system may be employed.

Instructions for the operating system, the object-oriented programming system, and applications or programs are located on storage devices, such as HDD 526, and may be loaded into main memory 508 for execution by processing unit 506. The processes for illustrative embodiments of the present invention may be performed by processing unit 506 using computer usable program code, which may be located in a memory such as, for example, main memory 508, ROM 524, or in one or more peripheral devices 526 and 530, for example.

A bus system, such as bus 538 or bus 540 as shown in FIG. 5, may be comprised of one or more buses. Of course, the bus system may be implemented using any type of communication fabric or architecture that provides for a transfer of data between different components or devices attached to the fabric or architecture. A communication unit, such as modem 522 or network adapter 512 of FIG. 5, may include one or more devices used to transmit and receive data. A memory may be, for example, main memory 508, ROM 524, or a cache such as found in NB/MCH 502 in FIG. 5.

As mentioned above, in some illustrative embodiments the mechanisms of the illustrative embodiments may be implemented as application specific hardware, firmware, or the like, application software stored in a storage device, such as HDD 526 and loaded into memory, such as main memory 508, for executed by one or more hardware processors, such as processing unit 506, or the like. As such, the computing device shown in FIG. 5 becomes specifically configured to implement the mechanisms of the illustrative embodiments and specifically configured to perform the operations and generate the outputs described hereafter with regard to the computer aided disease detection with masked attention.

Those of ordinary skill in the art will appreciate that the hardware in FIG. 5 may vary depending on the implementation. Other internal hardware or peripheral devices, such as flash memory, equivalent non-volatile memory, or optical disk drives and the like, may be used in addition to or in place of the hardware depicted in FIG. 5. Also, the processes of the illustrative embodiments may be applied to a multiprocessor data processing system, other than the SMP system mentioned previously, without departing from the spirit and scope of the present invention.

Moreover, the data processing system 500 may take the form of any of a number of different data processing systems including client computing devices, server computing devices, a tablet computer, laptop computer, telephone or other communication device, a personal digital assistant (PDA), or the like. In some illustrative examples, data processing system 500 may be a portable computing device that is configured with flash memory to provide non-volatile memory for storing operating system files and/or user-generated data, for example. Essentially, data processing system 500 may be any known or later developed data processing system without architectural limitation.

As noted above, it should be appreciated that the illustrative embodiments may take the form of an entirely hardware embodiment, an entirely software embodiment or an embodiment containing both hardware and software elements. In one example embodiment, the mechanisms of the illustrative embodiments are implemented in software or program code, which includes but is not limited to firmware, resident software, microcode, etc.

A data processing system suitable for storing and/or executing program code will include at least one processor coupled directly or indirectly to memory elements through a communication bus, such as a system bus, for example. The memory elements can include local memory employed during actual execution of the program code, bulk storage, and cache memories which provide temporary storage of at least some program code in order to reduce the number of times code must be retrieved from bulk storage during execution. The memory may be of various types including, but not limited to, ROM, PROM, EPROM, EEPROM, DRAM, SRAM, Flash memory, solid state memory, and the like.

Input/output or I/O devices (including but not limited to keyboards, displays, pointing devices, etc.) can be coupled to the system either directly or through intervening wired or wireless I/O interfaces and/or controllers, or the like. I/O devices may take many different forms other than conventional keyboards, displays, pointing devices, and the like, such as for example communication devices coupled through wired or wireless connections including, but not limited to, smart phones, tablet computers, touch screen devices, voice recognition devices, and the like. Any known or later developed I/O device is intended to be within the scope of the illustrative embodiments.

Network adapters may also be coupled to the system to enable the data processing system to become coupled to other data processing systems or remote printers or storage devices through intervening private or public networks. Modems, cable modems and Ethernet cards are just a few of the currently available types of network adapters for wired communications. Wireless communication based network adapters may also be utilized including, but not limited to, 802.11 a/b/g/n wireless communication adapters, Bluetooth wireless adapters, and the like. Any known or later developed network adapters are intended to be within the spirit and scope of the present invention.

The description of the present invention has been presented for purposes of illustration and description, and is not intended to be exhaustive or limited to the invention in the form disclosed. Many modifications and variations will be apparent to those of ordinary skill in the art without departing from the scope and spirit of the described embodiments. The embodiment was chosen and described in order to best explain the principles of the invention, the practical application, and to enable others of ordinary skill in the art to understand the invention for various embodiments with various modifications as are suited to the particular use contemplated. The terminology used herein was chosen to best explain the principles of the embodiments, the practical application or technical improvement over technologies found in the marketplace, or to enable others of ordinary skill in the art to understand the embodiments disclosed herein.

What is claimed is:

1. A method, in a data processing system, for computer aided disease detection with masked attention, the method comprising:
   generating, by a candidate generator, a set of candidate three-dimensional image patches from an input volume;
   classifying, by a candidate classifier, the set of candidate three-dimensional image patches as containing or not containing disease, wherein classifying the set of candidate three-dimensional image patches comprises:
      generating an attention mask for each given candidate three-dimensional image patch within the set of candidate three-dimensional image patches to form a set of attention masks;
      applying the set of attention masks to the set of candidate three-dimensional image patches to form a set of masked image patches; and
      classifying the set of masked image patches as containing or not containing the disease,
   wherein the candidate classifier applies soft attention and hard attention to the three-dimensional image patches such that distinctive image regions are highlighted proportionally to their contribution to classification while completely removing image regions that may cause confusion, wherein generating the set of candidate three-dimensional image patches comprises decomposing the input volume into a set of image slabs and applying a first neural network to the set of image slabs to segment the set of image slabs into the set of candidate three-dimensional image patches.

2. The method of claim 1, wherein the first neural network is a two-dimensional UNet neural network.

3. The method of claim 1, wherein generating the attention mask for each given candidate three-dimensional image patch comprises applying a second neural network and a rectified linear unit (ReLU) to the given candidate three-dimensional image patch.

4. The method of claim 3, wherein the rectified linear unit applies an ReLU function A(x) as follows:

$$A(x) = \begin{cases} M(x) & \text{if } M(x) \geq 0 \\ 0 & \text{otherwise} \end{cases},$$

where M(x) is a transform map $M \in \mathbb{R}^{L \times L \times L}$, L×L×L is the size of the input image patch.

5. The method of claim 1, wherein a applying the set of attention masks to the set of candidate three-dimensional image patches comprises applying element-wise multiplication.

6. The method of claim 3, wherein classifying the set of masked image patches comprises applying a third neural network to the set of masked image patches.

7. The method of claim 6, wherein the third neural network is a three-dimensional squeezeNet.

8. The method of claim 6, wherein the second neural network and the third neural network are trained jointly.

9. The method of claim 1, further comprising classifying the input volume as containing the disease if and only if at least one of the set of masked image patches is classified as containing the disease.

10. A computer program product comprising a non-transitory computer readable medium having a computer readable program stored therein, wherein the computer readable program, when executed on a computing device, causes the computing device to:
generate, by a candidate generator, a set of candidate three-dimensional image patches from an input volume;
classify, by a candidate classifier, the set of candidate three-dimensional image patches as containing or not containing disease, wherein classifying the set of candidate three-dimensional image patches comprises:
generating an attention mask for each given candidate three-dimensional image patch within the set of candidate three-dimensional image patches to form a set of attention masks;
applying the set of attention masks to the set of candidate three-dimensional image patches to form a set of masked image patches; and
classifying the set of masked image patches as containing or not containing the disease,
wherein the candidate classifier applies soft attention and hard attention to the three-dimensional image patches such that distinctive image regions are highlighted proportionally to their contribution to classification while completely removing image regions that may cause confusion, wherein generating the set of candidate three-dimensional image patches comprises decomposing the input volume into a set of image slabs and applying a first neural network to the set of image slabs to segment the set of image slabs into the set of candidate three-dimensional image patches.

11. The computer program product of claim 10, wherein generating the attention mask for each given candidate three-dimensional image patch comprises applying a second neural network and a rectified linear unit (ReLU) to the given candidate three-dimensional image patch.

12. The computer program product of claim 11, wherein the rectified linear unit applies an ReLU function A(x) as follows:

$$A(x) = \begin{cases} M(x) & \text{if } M(x) \geq 0 \\ 0 & \text{otherwise} \end{cases},$$

where M(x) is a transform map $M \in \mathbb{R}^{L \times L \times L}$, L×L×L is the size of the input image patch.

13. The computer program product of claim 10, wherein a applying the set of attention masks to the set of candidate three-dimensional image patches comprises applying element-wise multiplication.

14. The computer program product of claim 13, wherein classifying the set of masked image patches comprises applying a third neural network to the set of masked image patches.

15. The computer program product of claim 14, wherein the third neural network is a three-dimensional squeezeNet.

16. The computer program product of claim 14, wherein the second neural network and the third neural network are trained jointly.

17. The computer program product of claim 10, further comprising classifying the input volume as containing the disease if and only if at least one of the set of masked image patches is classified as containing the disease.

18. An apparatus comprising:
a processor; and
a memory coupled to the processor, wherein the memory comprises instructions which, when executed by the processor, cause the processor to:
generate, by a candidate generator, a set of candidate three-dimensional image patches from an input volume;
classify, by a candidate classifier, the set of candidate three-dimensional image patches as containing or not containing disease, wherein classifying the set of candidate three-dimensional image patches comprises:
generating an attention mask for each given candidate three-dimensional image patch within the set of candidate three-dimensional image patches to form a set of attention masks;
applying the set of attention masks to the set of candidate three-dimensional image patches to form a set of masked image patches; and
classifying the set of masked image patches as containing or not containing the disease,
wherein the candidate classifier applies soft attention and hard attention to the three-dimensional image patches such that distinctive image regions are highlighted proportionally to their contribution to classification while completely removing image regions that may cause confusion, wherein generating the set of candidate three-dimensional image patches comprises decomposing the input volume into a set of image slabs and applying a first neural network to the set of image slabs to segment the set of image slabs into the set of candidate three-dimensional image patches.

19. The apparatus of claim 18, wherein generating the attention mask for each given candidate three-dimensional image patch comprises applying a second neural network and a rectified linear unit (ReLU) to the given candidate three-dimensional image patch.

20. The apparatus of claim 19, wherein classifying the set of masked image patches comprises applying a third neural network to the set of masked image patches.

* * * * *